United States Patent
Stoll, Jr. et al.

(10) Patent No.: US 9,072,509 B2
(45) Date of Patent: Jul. 7, 2015

(54) TOGGLE BOLT SUTURE ANCHOR KIT

(75) Inventors: Edward Jordan Stoll, Jr., Boulder, CO (US); Kyle Craig Pilgeram, San Jose, CA (US)

(73) Assignees: Howmedica Osteonics Corp., Mahwah, NJ (US); Stoll Family Enterprises, Ltd., Boulder, CO (US)

( * ) Notice: Subject to any disclaimer, the term of this patent is extended or adjusted under 35 U.S.C. 154(b) by 560 days.

(21) Appl. No.: 12/682,324

(22) PCT Filed: Oct. 9, 2008

(86) PCT No.: PCT/US2008/079277
§ 371 (c)(1),
(2), (4) Date: Sep. 7, 2010

(87) PCT Pub. No.: WO2009/049002
PCT Pub. Date: Apr. 16, 2009

(65) Prior Publication Data
US 2011/0125189 A1 May 26, 2011

Related U.S. Application Data

(60) Provisional application No. 60/979,655, filed on Oct. 12, 2007.

(51) Int. Cl.
*A61B 17/04* (2006.01)
*F16B 13/08* (2006.01)

(52) U.S. Cl.
CPC .......... *A61B 17/0401* (2013.01); *F16B 13/0808* (2013.01); *A61B 2017/0404* (2013.01); *A61B 2017/0409* (2013.01); *A61B 2017/0414* (2013.01)

(58) Field of Classification Search
CPC ............... A61B 2017/0409; A61B 2017/0414; A61B 2017/0417; A61B 17/0401; A61F 2/0811
USPC ............... 606/232; 623/13.11–13.2; 411/344, 411/340; 403/60, 117, 118, 52, 164, 119
See application file for complete search history.

(56) References Cited

U.S. PATENT DOCUMENTS

| 860,636 A | * | 7/1907 | Church ......................... 411/113 |
| 2,485,531 A | | 10/1949 | Dzus et al. |
| 3,332,118 A | * | 7/1967 | Temple et al. ................. 403/353 |
| 3,976,079 A | | 8/1976 | Samuels et al. |
| 4,075,924 A | * | 2/1978 | McSherry et al. ............. 411/112 |

(Continued)

FOREIGN PATENT DOCUMENTS

WO 2006/130693 A2 12/2006

OTHER PUBLICATIONS

Case No. 2:07-CV-335-TJW, Doc. 82, *Smith & Nephew, Inc. v. Arthrex, Inc.*, Infringment of USPN 5,306,301 and 5,645,588, 47 pages, Nov. 20, 2009.

(Continued)

*Primary Examiner* — Gregory Anderson
*Assistant Examiner* — Christopher L Templeton
(74) *Attorney, Agent, or Firm* — Lerner, David, Littenberg, Krumholz & Mentlik, LLP

(57) ABSTRACT

In one embodiment, the present invention includes a toggle bolt suture anchor system including a toggle bolt suture anchor having at least one groove; and a toggle bolt delivery device having at least one push pin for pivotable interconnection with the groove.

16 Claims, 14 Drawing Sheets

(56) References Cited

U.S. PATENT DOCUMENTS

| | | | | |
|---|---|---|---|---|
| 4,265,231 | A | 5/1981 | Scheller, Jr. et al. | |
| 4,294,156 | A * | 10/1981 | McSherry et al. | 411/345 |
| 4,298,298 | A * | 11/1981 | Pontone | 411/342 |
| 4,439,079 | A * | 3/1984 | Losada | 411/345 |
| 4,590,928 | A | 5/1986 | Hunt et al. | |
| 4,650,386 | A * | 3/1987 | McSherry et al. | 411/340 |
| 4,782,451 | A | 11/1988 | Mazzarella et al. | |
| 5,002,546 | A | 3/1991 | Romano | |
| 5,030,219 | A | 7/1991 | Matsen, III et al. | |
| 5,139,520 | A | 8/1992 | Rosenberg | |
| 5,242,457 | A | 9/1993 | Akopov et al. | |
| 5,269,809 | A | 12/1993 | Hayhurst et al. | |
| 5,306,301 | A | 4/1994 | Graf et al. | |
| 5,374,269 | A | 12/1994 | Rosenberg | |
| 5,395,188 | A | 3/1995 | Bailey et al. | |
| 5,409,490 | A | 4/1995 | Ethridge | |
| 5,437,677 | A | 8/1995 | Shearer et al. | |
| 5,454,821 | A | 10/1995 | Harm et al. | |
| 5,464,425 | A | 11/1995 | Skiba | |
| 5,484,451 | A | 1/1996 | Akopov et al. | |
| 5,496,348 | A | 3/1996 | Bonutti | |
| 5,522,846 | A | 6/1996 | Bonutti | |
| 5,573,543 | A | 11/1996 | Akopov et al. | |
| 5,584,835 | A | 12/1996 | Greenfield | |
| 5,628,740 | A | 5/1997 | Mullane | |
| 5,645,588 | A | 7/1997 | Graf et al. | |
| 5,733,307 | A | 3/1998 | Dinsdale | |
| 5,769,894 | A | 6/1998 | Ferragamo | |
| 5,868,789 | A | 2/1999 | Huebner | |
| 5,921,986 | A | 7/1999 | Bonutti | |
| 6,010,525 | A | 1/2000 | Bonutti et al. | |
| 6,045,574 | A | 4/2000 | Thal | |
| 6,056,752 | A | 5/2000 | Roger | |
| 6,068,648 | A | 5/2000 | Cole et al. | |
| 6,099,568 | A | 8/2000 | Simonian et al. | |
| 6,110,207 | A | 8/2000 | Eichhorn et al. | |
| 6,117,139 | A | 9/2000 | Shino | |
| 6,161,999 | A * | 12/2000 | Kaye et al. | 411/344 |
| 6,171,310 | B1 | 1/2001 | Giordano et al. | |
| 6,187,011 | B1 | 2/2001 | Torrie | |
| 6,267,767 | B1 | 7/2001 | Strobel et al. | |
| 6,287,065 | B1 | 9/2001 | Berlin | |
| 6,419,678 | B1 | 7/2002 | Asfora | |
| 6,440,134 | B1 * | 8/2002 | Zaccherotti et al. | 606/62 |
| 6,451,030 | B2 | 9/2002 | Li et al. | |
| 6,482,210 | B1 | 11/2002 | Skiba et al. | |
| RE37,963 | E | 1/2003 | Thal | |
| 6,517,542 | B1 | 2/2003 | Papay et al. | |
| 6,517,578 | B2 | 2/2003 | Hein | |
| 6,533,802 | B2 | 3/2003 | Bojarski et al. | |
| 6,547,800 | B2 | 4/2003 | Foerster et al. | |
| 6,562,071 | B2 | 5/2003 | Jarvinen | |
| 6,569,187 | B1 | 5/2003 | Bonutti et al. | |
| 6,638,279 | B2 | 10/2003 | Bonutti | |
| 6,641,596 | B1 | 11/2003 | Lizardi | |
| 6,641,597 | B2 | 11/2003 | Burkhart et al. | |
| 6,652,563 | B2 | 11/2003 | Dreyfuss | |
| 6,736,829 | B1 | 5/2004 | Li et al. | |
| 6,773,436 | B2 | 8/2004 | Donnelly | |
| 6,840,953 | B2 | 1/2005 | Martinek | |
| 6,923,824 | B2 | 8/2005 | Morgan et al. | |
| 7,037,324 | B2 | 5/2006 | Martinek | |
| 7,041,120 | B2 | 5/2006 | Li et al. | |
| 7,087,073 | B2 | 8/2006 | Bonutti | |
| 7,090,690 | B2 | 8/2006 | Foerster et al. | |
| 7,097,654 | B1 | 8/2006 | Freedland | |
| 7,108,710 | B2 | 9/2006 | Anderson | |
| 7,163,540 | B2 | 1/2007 | Martello | |
| 7,736,108 | B1 * | 6/2010 | Bruce et al. | 411/346 |
| 7,803,173 | B2 | 9/2010 | Burkhart et al. | |
| 7,819,898 | B2 | 10/2010 | Stone et al. | |
| 7,828,820 | B2 | 11/2010 | Stone et al. | |
| 7,875,057 | B2 | 1/2011 | Cook et al. | |
| 7,896,907 | B2 | 3/2011 | McDevitt et al. | |
| 7,934,506 | B2 | 5/2011 | Woodson et al. | |
| 8,109,965 | B2 | 2/2012 | Stone et al. | |
| 8,114,127 | B2 | 2/2012 | West, Jr. | |
| 8,128,669 | B2 | 3/2012 | Bonutti | |
| 8,147,514 | B2 | 4/2012 | Bonutti | |
| 8,231,674 | B2 | 7/2012 | Albertorio et al. | |
| 8,388,655 | B2 | 3/2013 | Fallin et al. | |
| 8,439,946 | B2 | 5/2013 | Miller et al. | |
| 8,506,596 | B2 | 8/2013 | Stone et al. | |
| 8,591,578 | B2 | 11/2013 | Albertorio et al. | |
| 8,613,756 | B2 | 12/2013 | Lizardi et al. | |
| 8,628,573 | B2 | 1/2014 | Roller et al. | |
| 8,672,969 | B2 | 3/2014 | Stone et al. | |
| 2001/0025181 | A1 | 9/2001 | Freedlan | |
| 2001/0041938 | A1 | 11/2001 | Hein | |
| 2002/0015629 | A1 * | 2/2002 | Ito | 411/340 |
| 2002/0019634 | A1 | 2/2002 | Bonutti | |
| 2002/0183762 | A1 | 12/2002 | Anderson et al. | |
| 2004/0002734 | A1 | 1/2004 | Fallin et al. | |
| 2004/0015171 | A1 | 1/2004 | Bojarski et al. | |
| 2004/0046009 | A1 | 3/2004 | Weisenberg et al. | |
| 2004/0127907 | A1 | 7/2004 | Dakin et al. | |
| 2004/0138706 | A1 | 7/2004 | Abrams et al. | |
| 2004/0236419 | A1 | 11/2004 | Milo | |
| 2004/0243128 | A1 | 12/2004 | Howland | |
| 2004/0243180 | A1 | 12/2004 | Donnelly et al. | |
| 2004/0260298 | A1 | 12/2004 | Kaiser et al. | |
| 2005/0038427 | A1 | 2/2005 | Perriello et al. | |
| 2005/0090827 | A1 | 4/2005 | Gedebou | |
| 2005/0234460 | A1 | 10/2005 | Miller | |
| 2005/0240189 | A1 | 10/2005 | Rousseau et al. | |
| 2005/0267479 | A1 | 12/2005 | Morgan et al. | |
| 2005/0273138 | A1 | 12/2005 | To et al. | |
| 2006/0052786 | A1 | 3/2006 | Dant et al. | |
| 2006/0122608 | A1 | 6/2006 | Fallin et al. | |
| 2006/0241656 | A1 | 10/2006 | Starksen et al. | |
| 2006/0265011 | A1 | 11/2006 | Bonutti | |
| 2006/0276841 | A1 | 12/2006 | Barbieri et al. | |
| 2006/0282081 | A1 | 12/2006 | Fanton et al. | |
| 2006/0282082 | A1 | 12/2006 | Fanton et al. | |
| 2007/0016208 | A1 | 1/2007 | Thornes | |
| 2007/0049944 | A1 | 3/2007 | Stone et al. | |
| 2007/0100353 | A1 | 5/2007 | Chudik | |
| 2007/0112338 | A1 | 5/2007 | Cohen et al. | |
| 2007/0118132 | A1 | 5/2007 | Culbert et al. | |
| 2007/0142835 | A1 | 6/2007 | Green et al. | |
| 2007/0225719 | A1 | 9/2007 | Stone et al. | |
| 2007/0233241 | A1 | 10/2007 | Graf et al. | |
| 2007/0270857 | A1 * | 11/2007 | Lombardo et al. | 606/72 |
| 2008/0046009 | A1 | 2/2008 | Albertorio et al. | |
| 2008/0086138 | A1 | 4/2008 | Stone et al. | |
| 2008/0109038 | A1 | 5/2008 | Steiner et al. | |
| 2008/0188935 | A1 | 8/2008 | Saylor et al. | |
| 2008/0255613 | A1 | 10/2008 | Kaiser et al. | |
| 2008/0287991 | A1 | 11/2008 | Fromm | |
| 2009/0018654 | A1 | 1/2009 | Schmieding et al. | |
| 2009/0105754 | A1 | 4/2009 | Sethi | |
| 2009/0204146 | A1 | 8/2009 | Kaiser et al. | |
| 2009/0234387 | A1 | 9/2009 | Miller et al. | |
| 2010/0004683 | A1 | 1/2010 | Hoof et al. | |
| 2010/0063541 | A1 | 3/2010 | Brunelle et al. | |
| 2010/0268273 | A1 | 10/2010 | Albertorio et al. | |
| 2011/0054526 | A1 | 3/2011 | Stone et al. | |
| 2011/0224764 | A1 | 9/2011 | Kulle | |
| 2011/0238113 | A1 | 9/2011 | Fanton et al. | |
| 2011/0301708 | A1 | 12/2011 | Stone et al. | |
| 2012/0116452 | A1 | 5/2012 | Stone et al. | |
| 2013/0023929 | A1 | 1/2013 | Sullivan et al. | |
| 2013/0090687 | A1 | 4/2013 | Lebeau et al. | |
| 2013/0103085 | A1 | 4/2013 | Hart et al. | |
| 2013/0123843 | A1 | 5/2013 | Chan et al. | |
| 2013/0131723 | A1 | 5/2013 | Snell et al. | |
| 2013/0238025 | A1 | 9/2013 | Howard et al. | |

(56) References Cited

U.S. PATENT DOCUMENTS

| | | |
|---|---|---|
| 2013/0253581 A1 | 9/2013 | Robison |
| 2013/0268073 A1 | 10/2013 | Albertorio et al. |
| 2013/0304120 A1 | 11/2013 | Stone et al. |
| 2013/0331885 A1 | 12/2013 | Stone et al. |
| 2013/0338710 A1 | 12/2013 | Heaven et al. |
| 2014/0025110 A1 | 1/2014 | Bonutti et al. |
| 2014/0194927 A1 | 7/2014 | Kaiser et al. |

OTHER PUBLICATIONS

Orthopedics Today, Point/Counterpoint ACL Reconstruction, Mar. 7, 2008.

Smith & Nephew, Endobutton CL, Fixation System, Knee Series, Technique Guide, 1999.

European Search Report, EP 12150748, May 8, 2012.

* cited by examiner

TOGGLE BOLT SUTURE ANCHOR KIT

CROSS-REFERENCE TO RELATED APPLICATIONS

The present application is a national phase entry under 35 U.S.C. §371 of International Application No. PCT/US2008/079277, filed Oct. 9, 2008, published in English, which claims priority from U.S. Provisional Patent Application No. 60/979,655, filed Oct. 12, 2007, all of which are incorporated herein by reference.

FIELD OF THE INVENTION

The present invention is related to kits and repair methods for soft tissue. In particular it is related to a kit comprising a toggle bolt suture anchor and a toggle bolt delivery device.

BACKGROUND OF THE INVENTION

Injuries to soft tissue and surrounding bones and joints are quite common. In particular, damage to the anterior cruciate ligament (ACL) and the acromioclavicular (AC) joint is very common, with damage to the AC joint being the second most common form of shoulder instability. In addition, injuries can occur to the distal biceps tendon and ankle syndesmosis. The prevalence of these types of injuries is increasing with the increased popularity of sports such as snowboarding. The injury usually occurs when the patient falls, striking the superior aspect of the shoulder with the arm adducted. The reaction force displaces the scapula downward, with progressive strain on the acromioclavicular ligaments, the coracoclavicular ligaments, followed by the deltoid and trapezius musculature and fascia. Treatment of this continuum of injuries depends upon the degree of injury of the aforementioned structures.

Various treatment methods have been proposed for the repair of injuries to the ACL and AC joints. Thornes in US Patent Application Publication No. 2007/0016208A1 describes a first suture anchor-suture-second suture anchor technique to reduce and internally fix the dislocation between the clavicle and the coracoid process. The apparatus of the invention comprises a first or second suture anchor in the form of a button. The button has a first aperture and a second aperture. A first or second suture anchor in the form of a washer is also presented. The washer has at least two flexible coupling-locating apertures. The washer also has a substantially centrally located bone screw-retaining aperture and at least two flexible coupling-locating apertures which are preferably counter-sunk so as to allow easier threading passage of the flexible coupling. In fixing the AC joint, the button and the washer are secured or pre-threaded together by means of a flexible coupling in the form of the first suture which is double looped through the first and second apertures of the button and the peripheral apertures of the washer. The first suture is fed through to an aperture of the washer; through the second and first apertures of the button; through the aperture, under the washer and back out the aperture; through the second and first apertures of the button again; and finally through the aperture of the washer. A needle with a second, pull-through suture is also looped through either the first or second apertures of the button. The second suture is looped through the first aperture of the button. A bone screw is used for engaging the washer with the coracoid process. The two trailing ends of the first suture are pulled to approximate the desired distance between the button and the washer, and hence reduce the interval between the clavicle and the coracoid process.

In another related application, Thornes (US Patent Application Publication No. US 2007/0179531A1) describes an acromioclavicular joint fixation technique which employs two fixation devices (for example, two buttons) joined by a continuous loop of flexible material. Each button is provided with at least one opening that allows the passage of the flexible material. In practicing the technique, a hole is drilled through the clavicle and the coracoid process using a cannulated drill. The cannulated drill is left in the clavicle and the coracoid. A suture is advanced by passing wire through the cannulated drill and the drill is subsequently removed. Two traction sutures are inserted from the oblong button of the fixation system through the wire loop of the suture passing wire. The suture passing wire is pulled to retrieve the two traction sutures out of the anterior/inferior cannula. The oblong button is advanced through the clavicle and the coracoid until it exits the coracoid base. Each of the traction sutures of the oblong button is pulled to flip the button onto the underside of the coracoid base, to secure the oblong button. The suture tails of the round button are pulled to advance the round button down to the surface of the clavicle. Lastly, the sutures are tied to stabilize the acromioclavicular joint.

Martello in U.S. Pat. No. 7,163,540 discloses a surgical anchor having one or more anchor holes distributed around the head of the anchor. The upper and lower apertures of each anchor hole are accessible to attach separate sutures to each of the anchor holes using conventional surgical techniques, i.e. curved needles. The inclined anchor holes allow a surgeon to efficiently attach soft tissue to the soft tissue securing anchor using preferred surgical tools without the necessity of using a multiplicity of specialized tools. The soft tissue securing anchor includes a head and securing end. The securing end may include any conventional means of securing a suture anchor into bone such as threads, barbs, fingers, toggle or molly bolts, and rivets. The head of the suture anchor may include a means for accommodating a drive tool such as a shaped head, tabs, flanges, channels, or one or more drive sockets such as a drive socket for securing the anchor. The soft tissue securing anchor is screwed into bone by applying a torque to soft tissue securing anchor using a conventional surgical drive tool inserted into the drive socket.

There are several problems associated with the aforementioned kits and methods. In particular, with respect to the AC joint, dissection under the coracoid process is required which leads to complications in the healing process. In addition, some of the methods require the use of sharp needles, suture or wires to pull the toggle into position. These instruments must be retrieved from the coracoid process without causing further damage to the coracoid process. Lastly, for those methods that use toggle bolts, the toggle must be pulled inferior to the coracoid which is difficult and potentially dangerous because of the anatomy, including the musculocutaneous nerve.

An object of the present invention is to provide a kit and method for repair of soft tissue, bone and joint damage.

Another object of the present invention is to provide a kit for the delivery of a graft in the repair of soft tissue, bone and joint damage.

Another object of the present invention is to provide a kit comprising a toggle bolt suture anchor and a toggle bolt delivery device where the toggle bolt suture and toggle bolt delivery device form an assembly.

Another object of the invention is to provide a kit comprising a toggle bolt suture anchor and toggle bolt delivery device where the toggle bolt delivery device enables the toggle bolt suture anchor to be pushed into position.

SUMMARY OF THE INVENTION

By the present invention, a toggle bolt suture anchor kit and method of using the kit is presented. The kit comprises a toggle bolt suture anchor and a toggle bolt delivery device. The toggle bolt suture anchor has at least one toggle bolt delivery device interconnection means. The toggle bolt delivery device has at least one toggle bolt suture anchor interconnection means. The toggle bolt delivery device enables the toggle bolt suture anchor to be pushed into its final position.

The toggle bolt suture anchor kit may be delivered as an assembly of the toggle bolt suture anchor and the toggle bolt delivery device. In this instance, the toggle bolt suture anchor is physically connected to the toggle bolt delivery device. The kit may or may not include at least one suture thread threaded through a pair of suture eyelets. In using the assembly, a leading edge of the toggle bolt suture anchor is pushed, using the toggle bolt delivery device, through a drill hole made either through bone, such as a clavicle, coracoid process, proximal radius, femur, tibia, or fibula. A trailing edge of the toggle bolt suture anchor is pushed into position using the toggle bolt delivery device, causing the toggle bolt suture anchor to become perpendicular to the drill hole. Once the toggle bolt suture anchor is perpendicular to the drill hole, the toggle bolt delivery device is disengaged from the toggle bolt, leaving the toggle bolt in position. The toggle bolt is secured by tying a suture thread, attached to the toggle bolt, in place, typically over bone.

Additional objects and advantages of the invention will be set forth in part in the description which follows, and in part, will be obvious from the description, or may be learned by practice of the invention. The objects and advantages of the invention will be obtained by means of instrumentalities in combinations particularly pointed out in the appended claims.

BRIEF DESCRIPTION OF THE DRAWINGS

The accompanying drawings illustrate a complete embodiment of the invention according to the best modes so far devised for the practical application of the principals thereof, and in which.

DETAILED DESCRIPTION OF THE PREFERRED EMBODIMENTS

The kit of the present invention comprises a toggle bolt suture anchor and a toggle bolt delivery device. The toggle bolt suture anchor and the toggle bolt delivery device are delivered as an assembly ready for use. This assembly enables the toggle bolt suture anchor to be pushed into position, rather than the prior art methods of pulling the toggle bolt suture anchor into position. It has been found that pushing the toggle bolt suture anchor into position offers several advantages over the prior art methods of pulling the toggle bolt into position. First, the need to dissect under various tissues, such as the coracoid process is eliminated. Secondly, there is no retrieval of sharp needles. Next, the need to use suture or wires to pull the toggle bolt suture anchor into position is greatly minimized and/or eliminated. As a result, the risk or amount of damage to surrounding structures and tissues, such as the coracoid process is greatly reduced. Although reference is made to the coracoid process, it is understood that the toggle bolt suture anchor kit may be used for other forms of surgery where a leading edge of the toggle bolt suture anchor is pushed, using the toggle bolt delivery device, through a drill hole made either through bone, such as a clavicle, coracoid process, proximal radius, femur, tibia, or fibula. A trailing edge of the toggle bolt suture anchor is pushed into position using the toggle bolt delivery device, causing the toggle bolt suture anchor to become perpendicular to the drill hole. Once the toggle bolt suture anchor is perpendicular to the drill hole, the toggle bolt delivery device is disengaged from the toggle bolt, leaving the toggle bolt in position.

Figure 1:
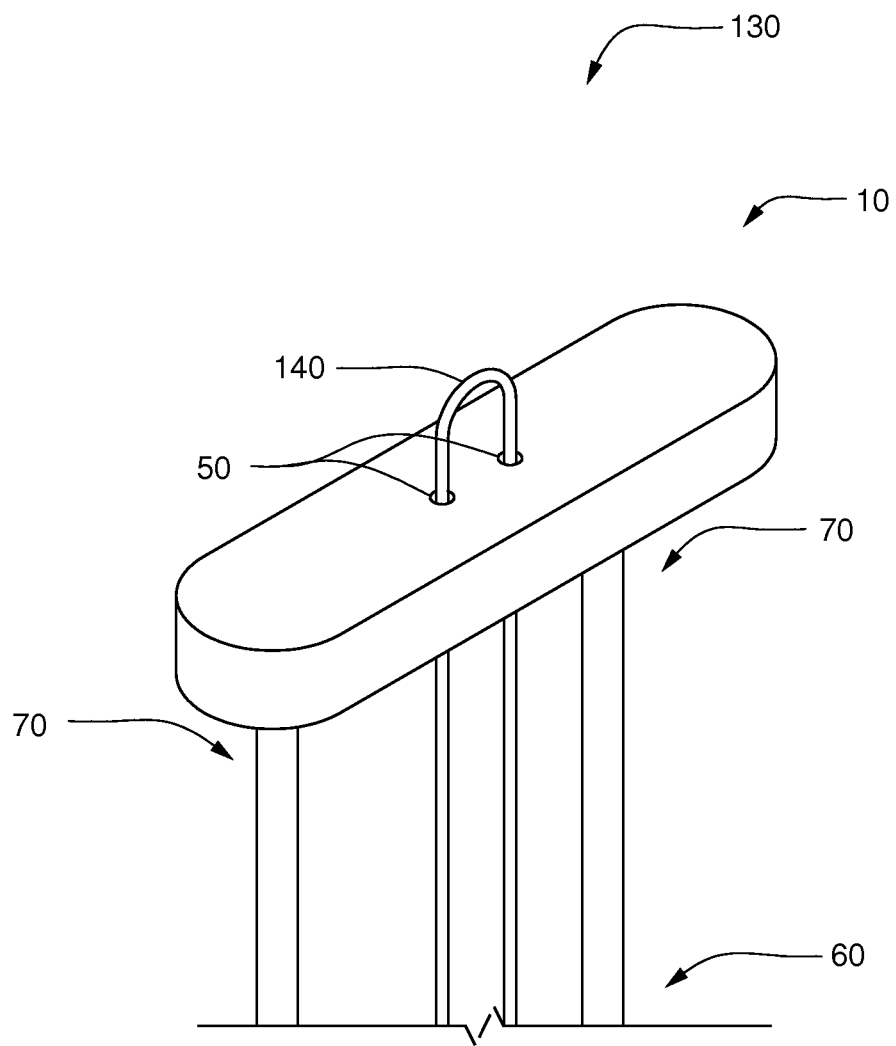
FIG. 1 is an isometric view of a first embodiment of the invention showing an assembly of the toggle bolt suture anchor and the toggle bolt delivery device.
Figure 2:
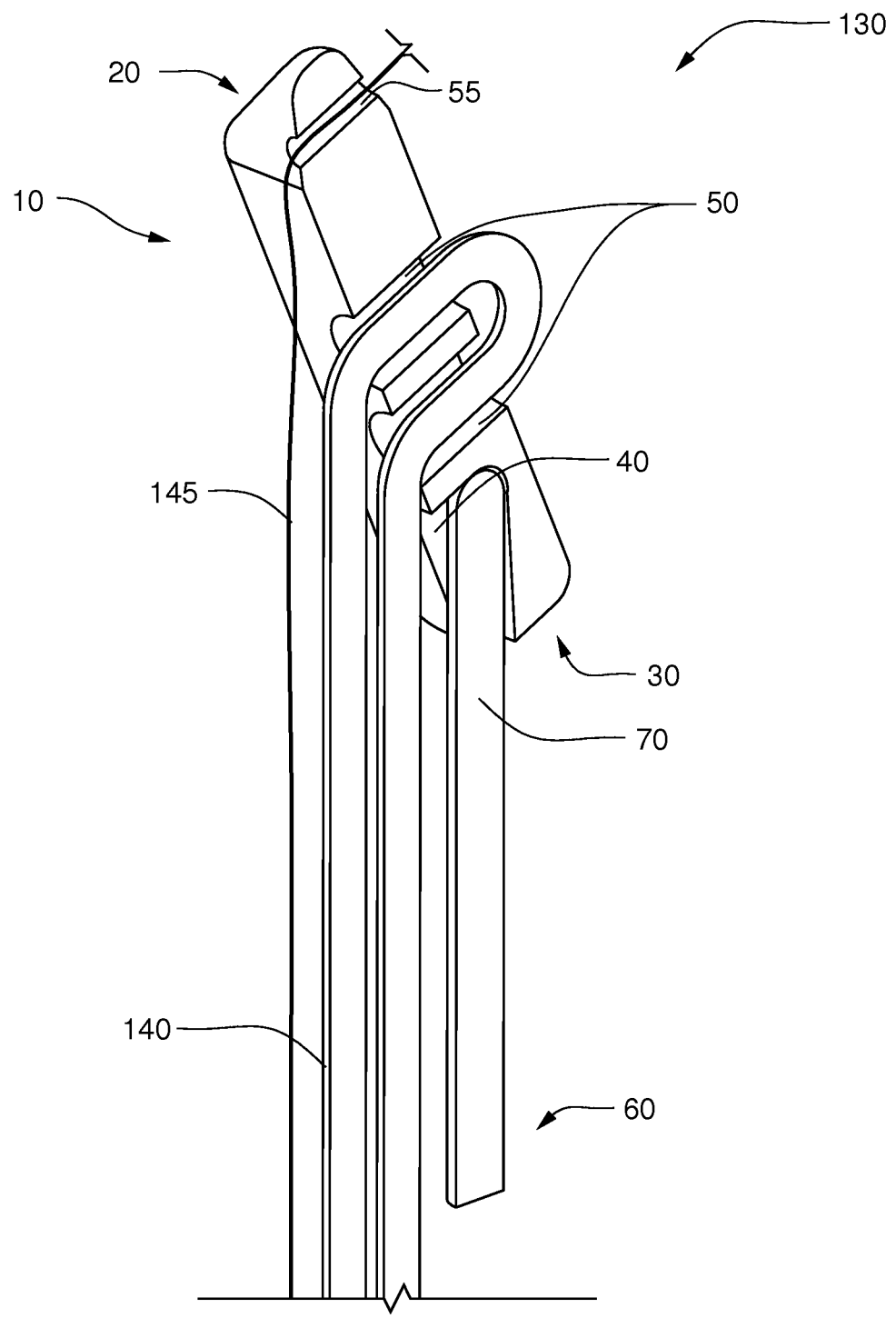
FIG. 2 is an isometric cross-sectional view of a second embodiment of the invention showing an alternative assembly of the toggle bolt suture anchor and the toggle bolt delivery device.
Figure 3:
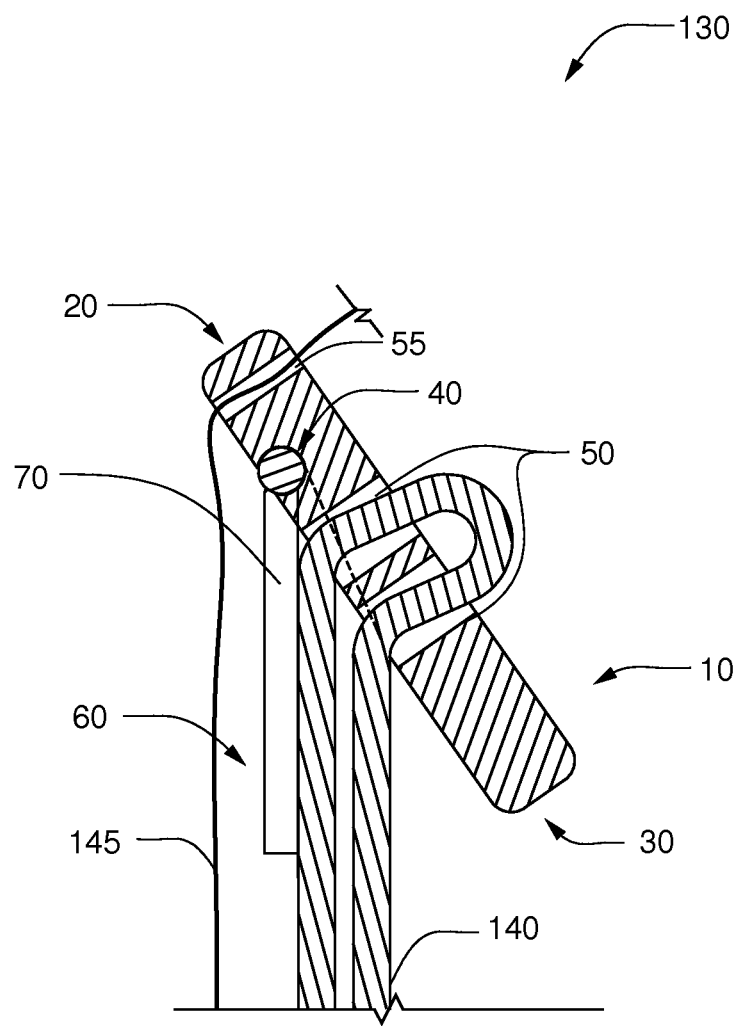
FIG. 3 is a cross-sectional view of a third embodiment of the invention showing an alternative assembly of the toggle bolt suture anchor and the toggle bolt delivery device.

Referring now to the figures where similar numbers are used to specify similar elements throughout, FIGS. 1, 2, and 3 depict three embodiments of the kit of the present invention where the toggle bolt suture anchor 10 forms an assembly 130 with the toggle bolt delivery device 60. In all three embodiments, the toggle bolt suture anchor 10 has at least one toggle bolt delivery device interconnection means 40 (not shown in FIG. 1) and the toggle bolt delivery device 60 has at least one toggle bolt suture anchor interconnection means 70. The interconnection between the toggle bolt suture anchor and the toggle bolt delivery device is established using any form of connection known to one of ordinary skill in the art. In one embodiment, the toggle bolt delivery device interconnection means 40 forms a male-female interconnection with the toggle bolt suture anchor interconnection means 70. In a second preferred embodiment, the toggle bolt delivery device interconnection means 40 forms an interlocking connection (such as a slide or pivot connection) with the toggle bolt suture anchor interconnection means 70. A third preferred embodiment involves the toggle bolt delivery device interconnection means forming a screw connection with the toggle bolt suture anchor interconnection means 70. Each of the figures depicts a further embodiment of the invention wherein the toggle bolt suture anchor 10 has a pair of suture eyelets 50. FIGS. 2 and 3 depict alternative embodiments wherein an additional suture eyelet 55 is positioned near a leading edge 20 of the toggle bolt suture anchor 10. As an alternative embodiment, the kit further includes at least one suture 140 threaded through the pair of suture eyelets 50. When the toggle bolt suture anchor 10 includes an additional suture eyelet 55 as shown in FIGS. 2 and 3, the kit may also include an additional suture 145 threaded through the additional suture eyelet 55. The toggle bolt suture anchor 10 may be pushed into position from either the leading 20 or trailing edge 30. When a suture 145 is positioned in the additional suture eyelet 55 in the leading edge 20, the suture 145 is pulled to help position the toggle bolt suture anchor 10 so it is perpendicular to a bone hole. The toggle bolt delivery device 60 is then removed by pulling the toggle bolt delivery device 60 and the suture 145.

Alternative embodiments of the toggle bolt suture anchor of the present invention are depicted in FIGS. 4A, 4B, 5, 6A, 6B, and 7. In general, each embodiment of the toggle bolt suture anchor 10 comprises an oblong body having a leading edge 20 and a trailing edge 30. At least one toggle bolt delivery device interconnection means 40 (FIGS. 6A, 6B, 7), 41 (FIGS. 4A, 4B, 5), 42 (FIGS. 4B, 5), 43 (FIG. 7), 45 (FIGS. 4A, 4B), 47 (FIG. 5) is positioned proximate to at least one edge of the toggle bolt suture anchor 10. A pair of suture eyelets 50 is positioned between the leading edge 20 and the trailing edge 30 of the toggle bolt suture anchor. Preferably, each suture eyelet is positioned equidistant from each edge 20, 30 of the toggle bolt suture anchor 10, although it is understood that the position of each suture eyelet may be optimized for a particular surgical application.

Figure 4A:
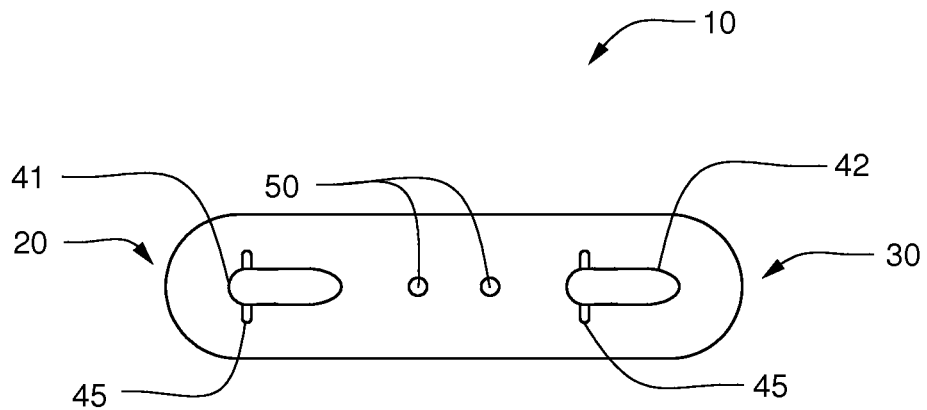
FIG. 4A is a bottom view of a first embodiment of a toggle bolt suture anchor of the present invention suitable for use in the assembly depicted in FIG. 1.
Figure 4B:
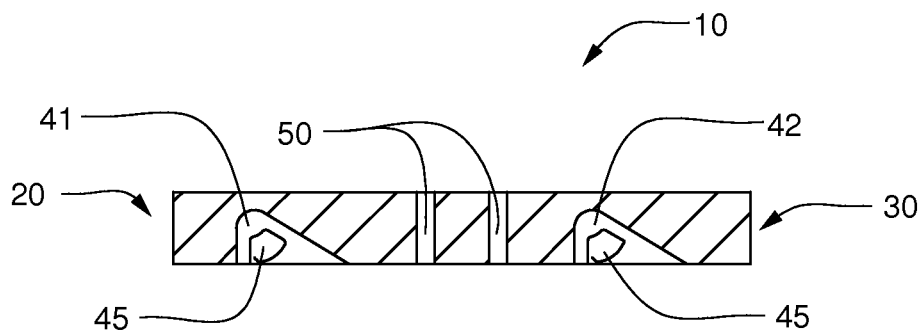
FIG. 4B is a cross-sectional view of the first embodiment of a toggle bolt suture anchor shown in FIG. 4A.

In a first embodiment of the toggle bolt suture anchor, shown in FIGS. 4A and 4B, the toggle bolt suture anchor 10 comprises an oblong body having a rounded leading edge 20 and a rounded trailing edge 30. In this embodiment, the toggle bolt delivery device interconnection means is defined by a first receptacle 41 (depicted as an indentation in the surface of the toggle bolt suture anchor 10) in the leading edge 20 of the toggle bolt suture anchor 10 and a second receptacle 42 (depicted as a second indentation in the surface of the toggle bolt suture anchor 10) in the trailing edge 30 of the toggle bolt suture anchor 10. Each receptacle 41, 42 is adapted to receive a toggle bolt delivery device (not shown). In this embodiment, the receptacles 41, 42 each have a means for engaging 45 with the toggle bolt delivery device (not shown). The means for engaging 45 with the toggle bolt delivery device enables the assembly to remain together until it is time to be released. This operates similar to a lock and key (or an interlocking connection). Positioned between the leading edge 20 and the trailing edge 30 of the toggle bolt suture anchor 10 is a pair of suture eyelets 50.

Figure 5:
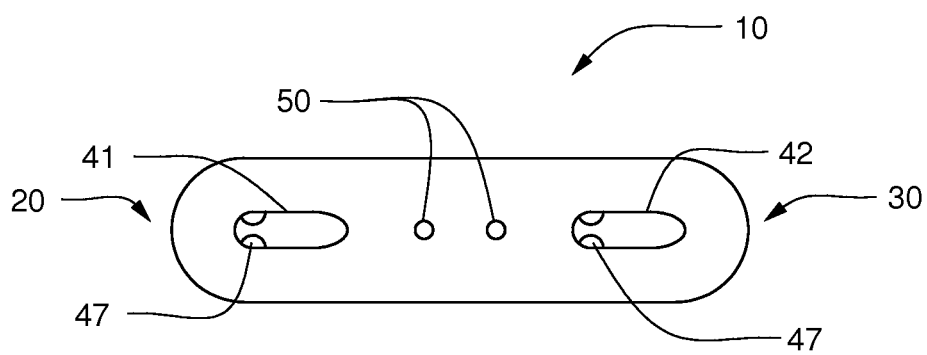
FIG. 5 is a bottom view of a second embodiment of the toggle bolt suture anchor of the present invention suitable for use in the assembly depicted in FIG. 1.

In a second embodiment of the toggle bolt suture anchor 10 (which is an alternative design of the first embodiment of the toggle bolt suture anchor), depicted in FIG. 5, the toggle bolt delivery device interconnection means is defined by a first receptacle 41 and a second receptacle 42. Each receptacle 41, 42 has at least one protrusion 47 on a surface thereof. A preferred embodiment is shown where a pair of protrusions 47 extend from each receptacle 41, 42. This protruded surface 47 mates with a toggle bolt delivery device having an indented end tip (not shown). In this instance, the toggle bolt suture anchor 10 snaps onto the tip of the toggle bolt delivery device (not shown), forming a male-female connection between the toggle bolt delivery device interconnection means 41, 42, 47 and a toggle bolt suture anchor interconnection means (not shown). A pair of suture eyelets 50 is positioned between each receptacle 41, 42.

Figure 6A:
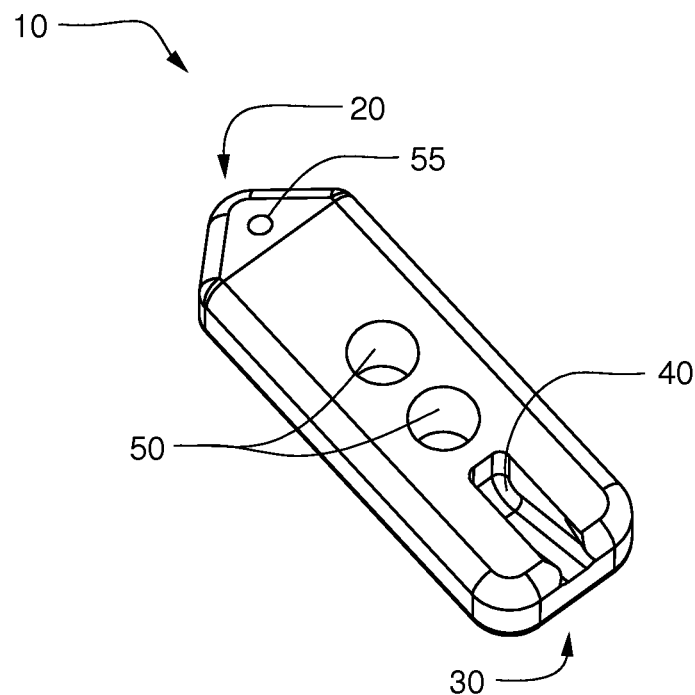
FIG. 6A is an isometric view of a third embodiment of the toggle bolt suture anchor of the present invention suitable for use in the assembly depicted in FIG. 2.
Figure 6B:
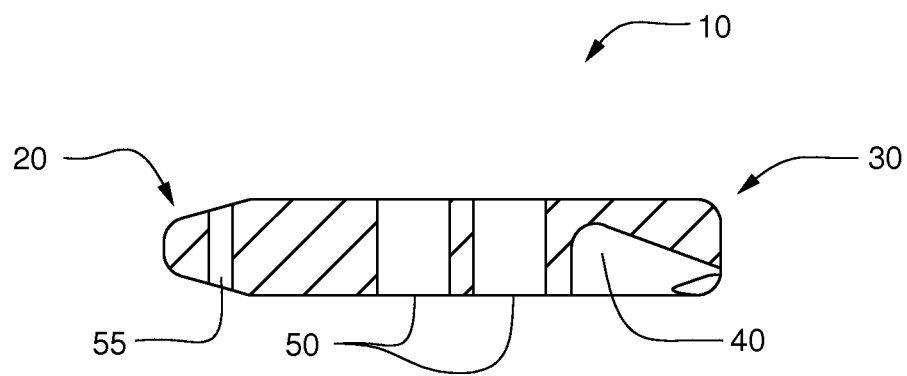
FIG. 6B is a cross-sectional view of the third embodiment of the toggle bolt suture anchor of the present invention.

A third embodiment of the toggle bolt suture anchor 10 is shown in FIGS. 6A and 6B. In this embodiment, the toggle bolt suture anchor 10 has a leading edge 20 that is angled. The toggle bolt delivery device interconnection means is a groove 40 positioned near the trailing edge 30 of the toggle bolt suture anchor 10. In this embodiment, the toggle bolt delivery device interconnection means 40 forms an interlocking connection with the toggle bolt suture anchor interconnection means (not shown) by sliding the toggle bolt suture anchor interconnection means (for example, a push pin, not shown) into the groove 40. A pair of suture eyelets 50 is positioned between the leading edge 20 and the trailing edge 30 of the toggle bolt suture anchor 10. A preferred embodiment is shown where a single suture eyelet 55 is positioned near the leading edge 20 of the toggle bolt suture anchor 10. This single suture eyelet 55 is threaded with either a suture or may be used to flip a graft into position.

Figure 7:
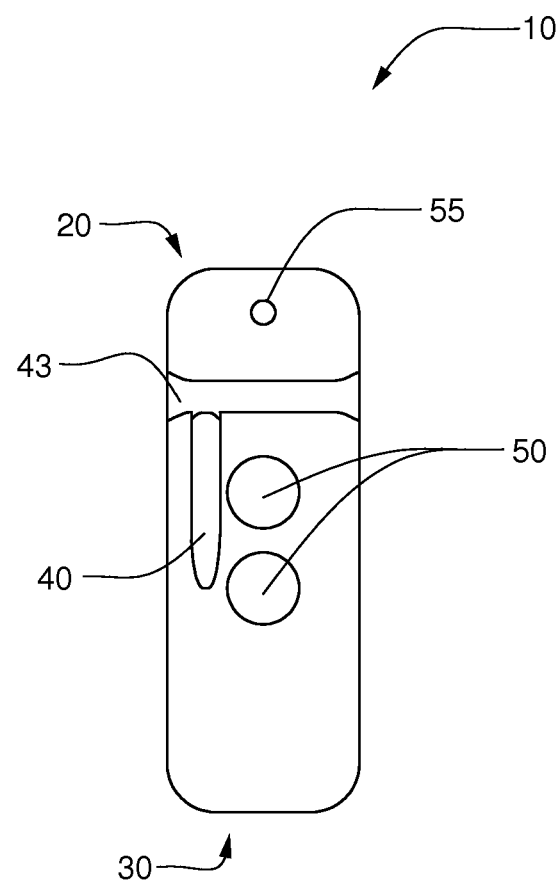
FIG. 7 is a bottom view of a fourth embodiment of the toggle bolt suture anchor of the present invention suitable for use in the assembly depicted in FIG. 3.

A fourth embodiment of the toggle bolt suture anchor 10 (which is an alternative embodiment of the third toggle bolt suture anchor) is shown in FIG. 7. In this embodiment, the toggle bolt suture anchor 10 has a leading edge 20 and a trailing edge 30 that has rounded corners. This configuration is to be considered as "rounded". The toggle bolt delivery device interconnection means is a first groove 40 positioned adjacent to the pair of suture eyelets 50 and near the leading edge 20 of the toggle bolt suture anchor 10. A second groove, serving as a pivot point 43 is positioned at a 90 degree angle with the first groove 40. (It is understood that the grooves 40, 43 are not require to have a 90 degree relationship to each other and that other angles or relationships may also be formed.) This design allows for the insertion of a toggle bolt suture anchor interconnection means (for example, a push pin) into the first and second grooves 40, 43 such that the toggle bolt suture anchor interconnection means acts as a lever and pivots as the toggle bolt suture anchor 10 is pushed and then flipped into position. A preferred embodiment is shown where a single suture eyelet 55 is positioned near the leading edge 20 of the toggle bolt suture anchor 10. This single suture eyelet 55 is threaded with either a suture or may be used to deliver a graft into position.

It is understood that various combinations of the toggle bolt delivery device interconnection means may be used and that the toggle bolt delivery device interconnection means may be modified using techniques known to one of ordinary skill in the art. For example, the toggle bolt delivery device interconnection means may be a receptacle with a protrusion positioned at the leading edge of the toggle bolt suture anchor and an indentation positioned at the trailing edge of the toggle bolt suture anchor or vice-versa. In addition, the toggle bolt delivery device interconnection means may be a threaded receptacle and the toggle bolt suture anchor interconnection means may be adapted for screwing into the threaded receptacle forming a screw connection (not shown).

Figure 8:
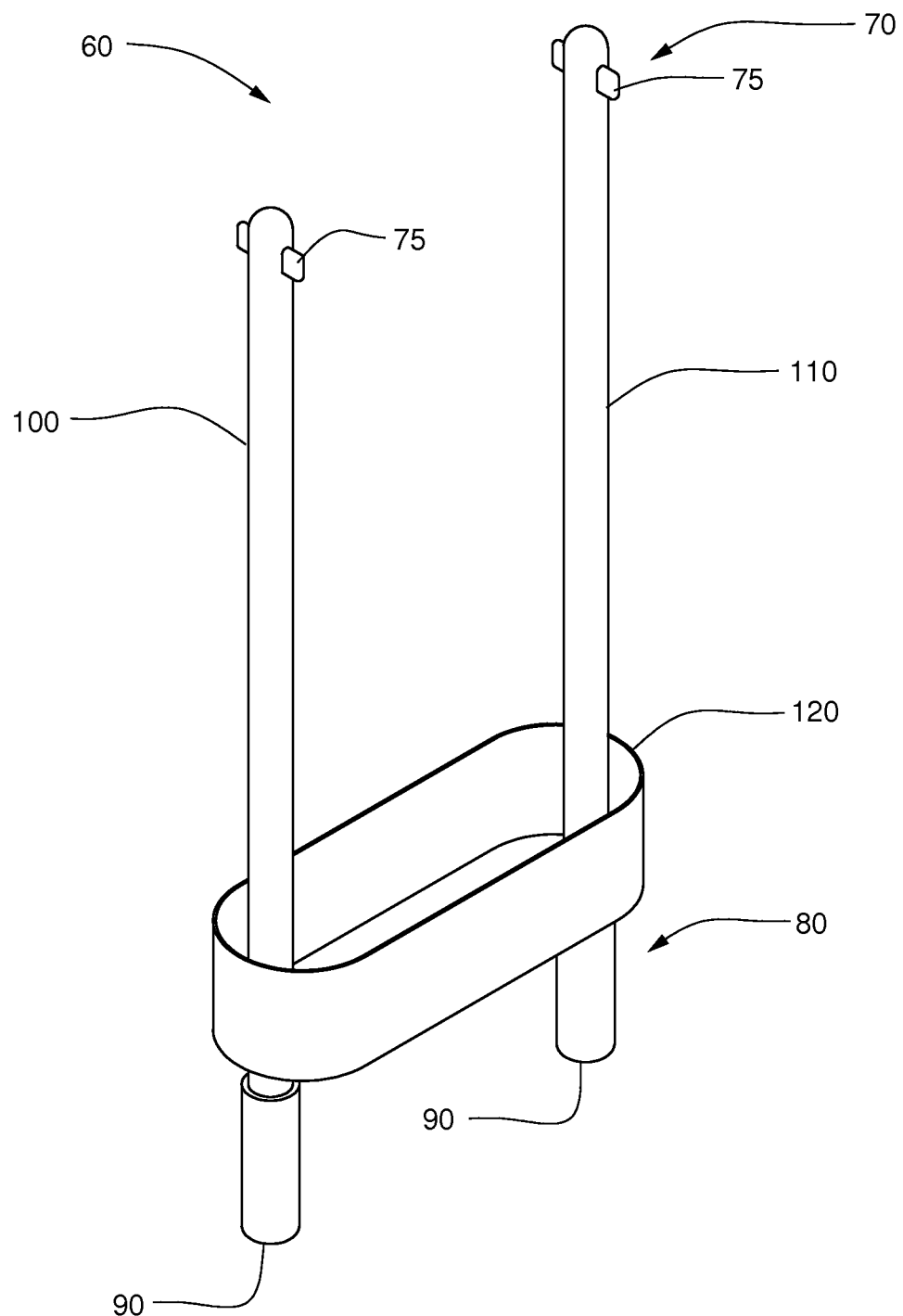
FIG. 8 is an isometric view of a toggle bolt delivery device suitable for use in the assembly depicted in FIG. 1.
Figure 9:
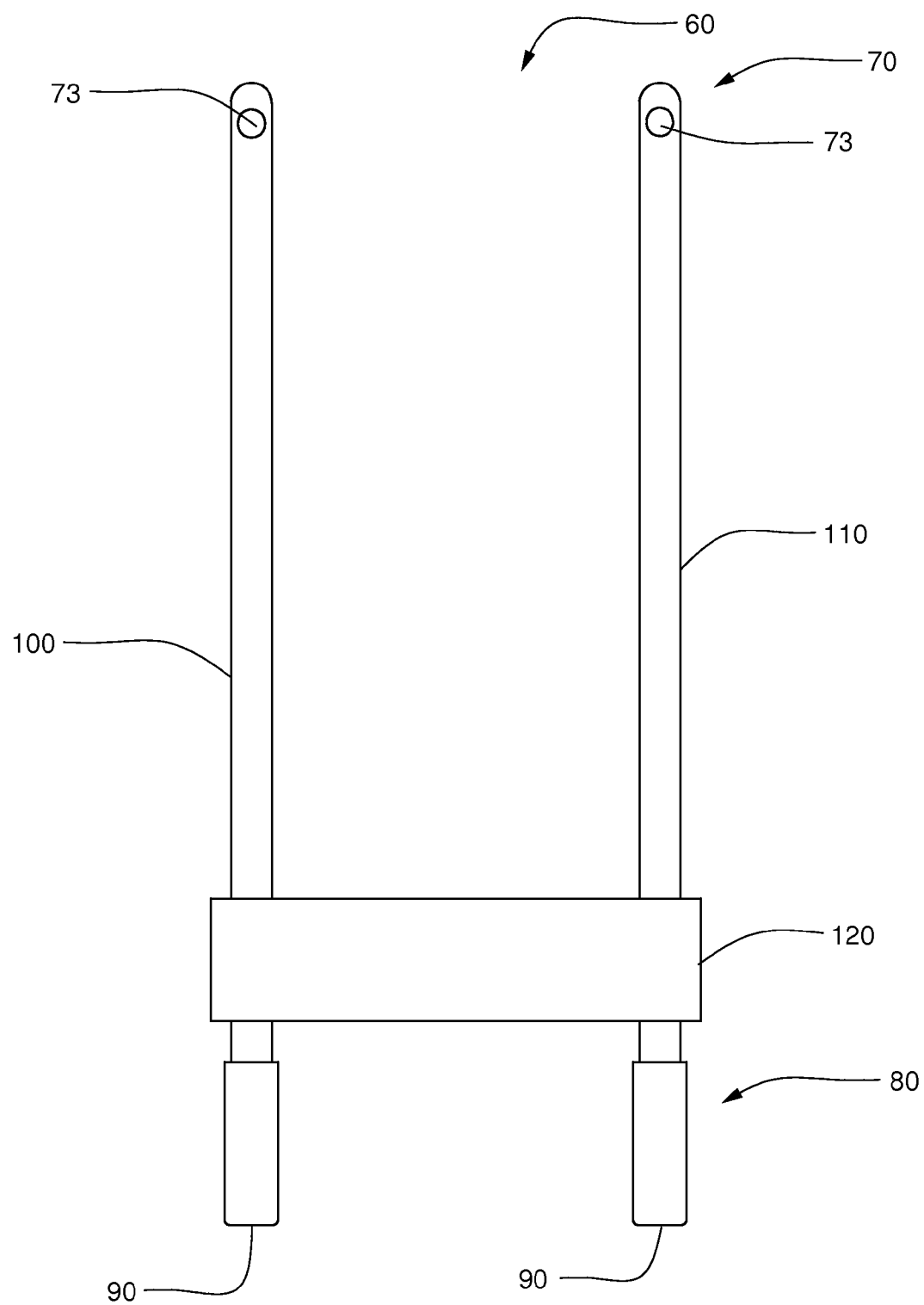
FIG. 9 is a front view of an alternate embodiment of the toggle bolt delivery device suitable for use in the assembly depicted in FIG. 1.

Two embodiments of the toggle bolt delivery device are depicted in FIGS. 8 and 9. In general, the toggle bolt delivery device 60 has at least one toggle bolt suture anchor interconnection means 70 adapted for interconnection with the toggle bolt delivery device interconnection means. The configuration of the toggle bolt delivery device interconnection means on the toggle bolt suture anchor will determine how the toggle bolt suture anchor interconnection means 70 of the toggle bolt delivery device 60 is configured. For example, FIG. 8 depicts the toggle bolt suture anchor interconnection means 70 as at least one semi-malleable wire (preferably a pair of semi-malleable wires 100, 110) having a protruded end 75. Whereas, FIG. 9 depicts the toggle bolt suture anchor interconnection means 70 as at least one semi-malleable wire (preferably a pair of semi-malleable wires 100, 110) having an indented end tip 73. In a further embodiment, a means for releasing the toggle bolt delivery device 90 from the toggle bolt suture anchor (not shown) is positioned at an end 80 opposite from the toggle bolt suture anchor interconnection means 70. The means for releasing the toggle bolt delivery device 90 is not as dependent upon the configuration of the toggle bolt delivery device interconnection means. Any means for releasing the toggle bolt delivery device may be suitable provided the means enables the toggle bolt suture anchor to be pushed into position. Such means include a plunger and a twisting means. For example, the toggle bolt suture anchor is pushed into position as a plunger is depressed, while flipping with a counter pulling motion on a suture to further position the toggle bolt suture anchor. The toggle bolt delivery device is released when the plunger is released. Most preferably, the toggle bolt suture anchor is released from the toggle bolt delivery device by depressing a plunger. Alternatively, the plunger is twisted prior to depressing.

As shown in FIGS. 8 and 9, the toggle bolt delivery device 60 is preferably comprised of first 100 and second 110 semi-malleable wires. Any semi-malleable wire material may be used such as metal or stainless steel but preferably, the semi-malleable wires are nitinol wires. The choice of the material is determined by the surgical application.

FIGS. 8 and 9 further depict a preferred embodiment where a disposable sleeve 120 is positioned between the toggle bolt suture anchor interconnection means 70 and the opposite end 80 of the toggle bolt delivery device 60. The disposable sleeve 120 surrounds the semi-malleable wires 100, 110 and the suture (not shown) to prevent entanglement during delivery of the toggle bolt suture anchor (not shown).

Figure 10:
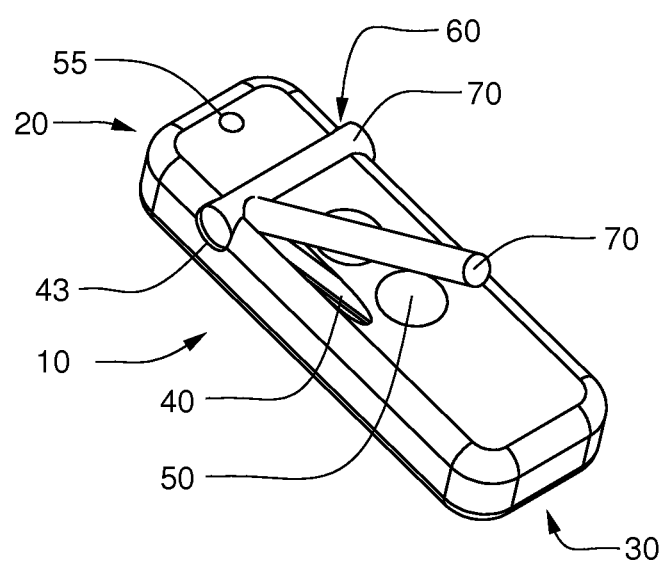
FIG. 10 is an isometric view of one embodiment of an assembly of the toggle bolt suture anchor with the toggle bolt delivery device suitable for use in the assembly depicted in FIG. 3.

FIG. 10 is a top view of one embodiment of an assembly of the toggle bolt suture anchor 10 with the toggle bolt delivery device 60. In this embodiment, the toggle bolt delivery device interconnection means is an L-shaped groove 40 having a pivot point 43. The toggle bolt suture anchor interconnection means 70 snaps into the toggle bolt delivery device interconnection means 40. The figure depicts the toggle bolt suture anchor interconnection means 70 as a lever (or push pin) which has been partially lifted to reveal one of the suture eyelets 50 located towards the trailing edge 30 of the toggle bolt suture anchor 10. An additional suture eyelet 55 is positioned near the leading edge 20 of the toggle bolt suture anchor 10. In use, the toggle bolt suture anchor interconnection means 70 acts as a lever and pivots as the toggle bolt suture anchor 10 is pushed and then flipped into position.

Figure 11A:
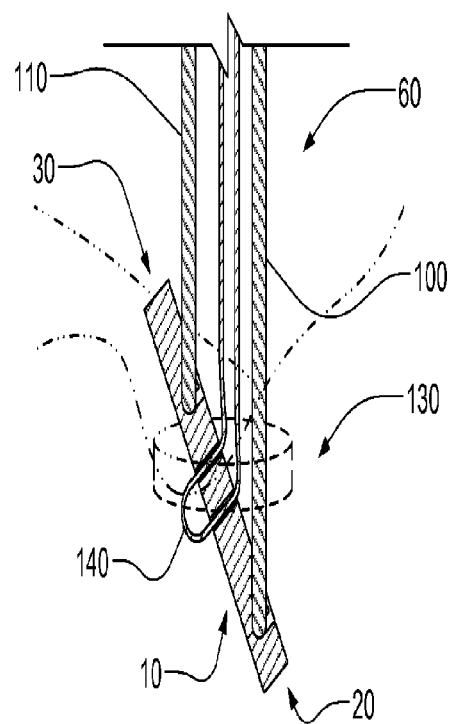
FIG. 11A is a cross-sectional view of the assembly of the toggle bolt suture anchor and toggle bolt delivery device shown in FIG. 1 as it is inserted through a drill hole in a bone.
Figure 11B:
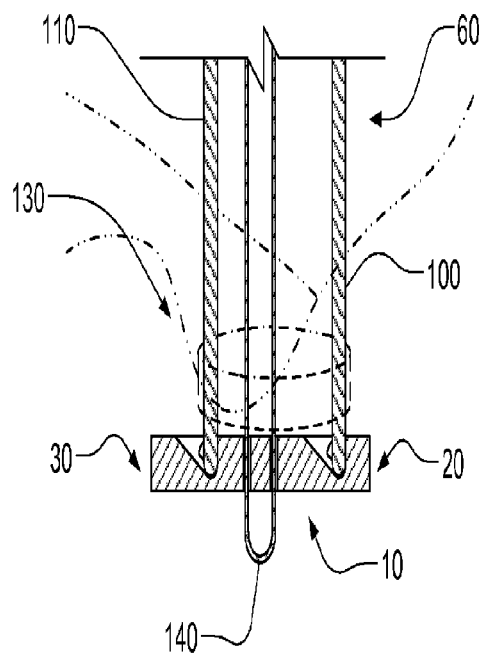
FIG. 11B is a cross-sectional view of the assembly of the toggle bolt suture anchor and toggle bolt delivery device shown in FIG. 1 after it is inserted through a drill hole and prior to removal of the toggle bolt delivery device from the toggle bolt.

FIGS. 11A and 11B depict the steps involved in positioning the toggle bolt suture anchor, using the assembly shown in FIG. 1, during a surgical procedure. The kit of the present invention comes with the toggle bolt suture anchor 10 attached to the toggle bolt delivery device 60 to form a toggle bolt assembly 130. The suture eyelets in the toggle bolt 10 are threaded with at least one suture thread 140. The surgical procedure is done thorough either standard incisions or limited incisions and arthroscopically assisted. In the standard incision surgery for an acromioclavicular repair, as shown in FIGS. 11A and 11B, the clavicle is exposed dorsally and the coracoid process identified. A drill hole is placed through the clavicle aiming towards the coracoid base. A second hole is drilled through the coracoid base. Visualized either directly or arthroscopically, the toggle bolt assembly 130 is inserted through the coracoid process by extending the leading edge 20 of the toggle bolt 10 such that the first semi-malleable wire 100 (which is attached near the leading edge 20 of the toggle bolt suture anchor 10) is longer than the second semi-malleable wire 110, which is attached to the trailing edge 30 of the toggle bolt suture anchor 10. Once the leading edge 20 of the toggle bolt suture anchor 10 is in position, the plunger (not shown) attached to the second semi-malleable wire 110 is released from a locked position. The plunger is then depressed, causing the trailing edge 30 of the toggle bolt suture anchor 10 to be pushed into position, causing the semi-malleable wires to be parallel, and placing the toggle bolt suture anchor perpendicular to the drill hole (see FIG. 11B). Once the toggle bolt suture anchor 10 is perpendicular to the drill hole, the toggle bolt delivery device consisting of the two semi-malleable wires is disengaged by pulling (or twisting) back, disconnecting the male-female connections, and leaving the toggle bolt in position. The toggle bolt is secured into position by tying the suture in place, typically over the dorsal clavicle, for example. Alternatively, it is understood that when performing an acromioclavicular repair, the toggle bolt is passed through a drill hole in the clavicle, then through the coracoid process, thus allowing the sutures to be in place for repositioning the clavicle and tying the sutures. It is also understood that although the surgical method described is for an acromioclavicular repair, the method would be similar for other types of surgeries where a drill hole is made through a bone, such as a clavicle, coracoid process, proximal radius, femur, tibia, or fibula.

Figure 12A:
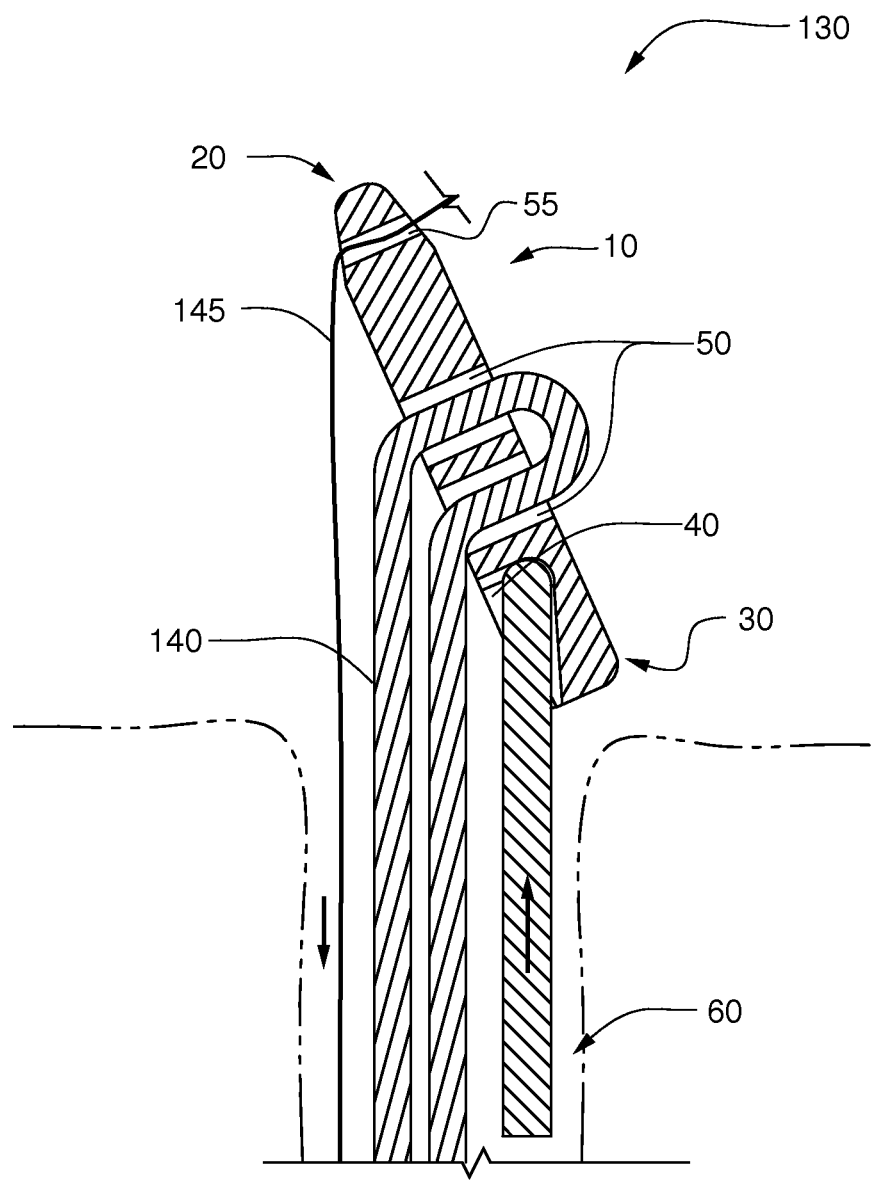
FIG. 12A is a cross-sectional view of the assembly of the toggle bolt suture anchor and toggle bolt delivery device shown in FIG. 2 as it is inserted through a drill hole in a bone.
Figure 12B:
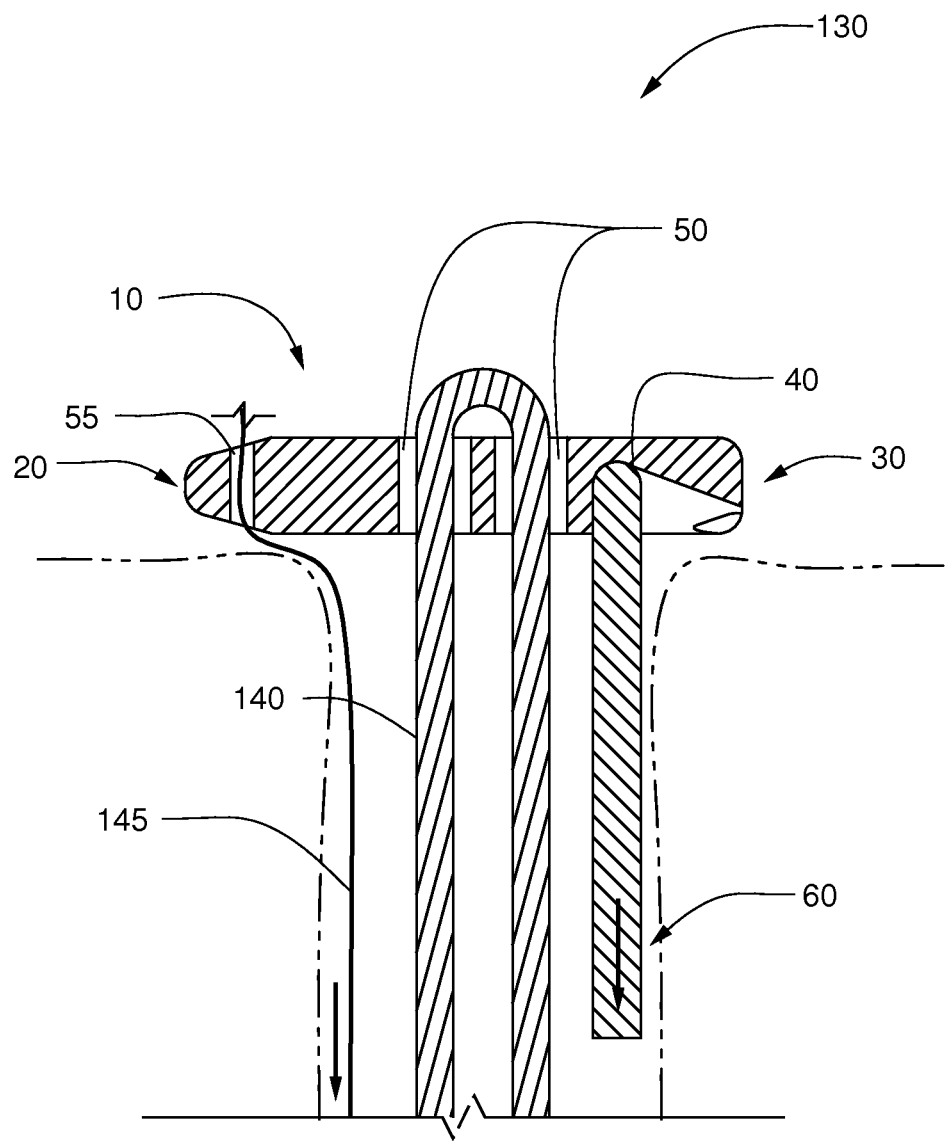
FIG. 12B is a cross-sectional view of the assembly of the toggle bolt suture anchor and toggle bolt delivery device shown in FIG. 2 after it is inserted through a drill hole and prior to removal of the toggle bolt delivery device from the toggle bolt.

FIGS. 12A and 12B depict the steps involved in positioning the toggle bolt suture anchor, using the assembly shown in FIG. 2, during a surgical procedure. The kit of the present invention comes with the toggle bolt suture anchor 10 attached to the toggle bolt delivery device 60 to form a toggle bolt assembly 130. The suture eyelets 50 in the toggle bolt suture anchor 10 are threaded with at least one suture thread 140. An additional suture eyelet 55 is threaded with a suture thread 145. The surgical procedure is done through either standard incisions or limited incisions and arthroscopically assisted. In the standard incision surgery, a drill hole is placed through the bone aiming towards the coracoid base. A second hole is drilled through the coracoid base. Visualized either directly or arthroscopically, the toggle bolt assembly 130 is inserted through the coracoid base by extending the leading edge 20 of the toggle bolt suture anchor 10 such that the suture 145 threaded through the single suture eyelet 55 (which is attached near the leading edge 20 of the toggle bolt suture anchor 10) is longer than the toggle bolt delivery device 60, which is attached to the trailing edge 30 of the toggle bolt suture anchor 10 at the toggle bolt delivery device interconnection means (a groove) 40. The toggle bolt delivery device 60 (for example a push pin) is used to push the toggle bolt assembly 130 into position by moving along a pivot point in a groove 40, causing the leading edge 20 and the trailing edge 30 of the toggle bolt suture anchor 10 to be pushed into position. In this embodiment, the lead suture 145 may be pulled to flip the trailing edge 30 of the toggle bolt suture anchor 10 into a final position where the sutures 140, 145 are parallel and the toggle bolt suture anchor 10 is perpendicular to the drill hole (see FIG. 12B). Once the toggle bolt suture anchor 10 is perpendicular to the drill hole, the toggle bolt delivery device is disengaged by pulling (or twisting) back, disconnecting the interlocking connection, and leaving the toggle bolt in position. The toggle bolt is secured into position by tying the suture in place, typically over a bone, for example. It is also understood that although the surgical method described is for an acromioclavicular repair, the method would be similar for other types of surgeries where a drill hole is made through a bone, such as a clavicle, coracoid process, proximal radius, femur, tibia, or fibula.

Figure 13A:
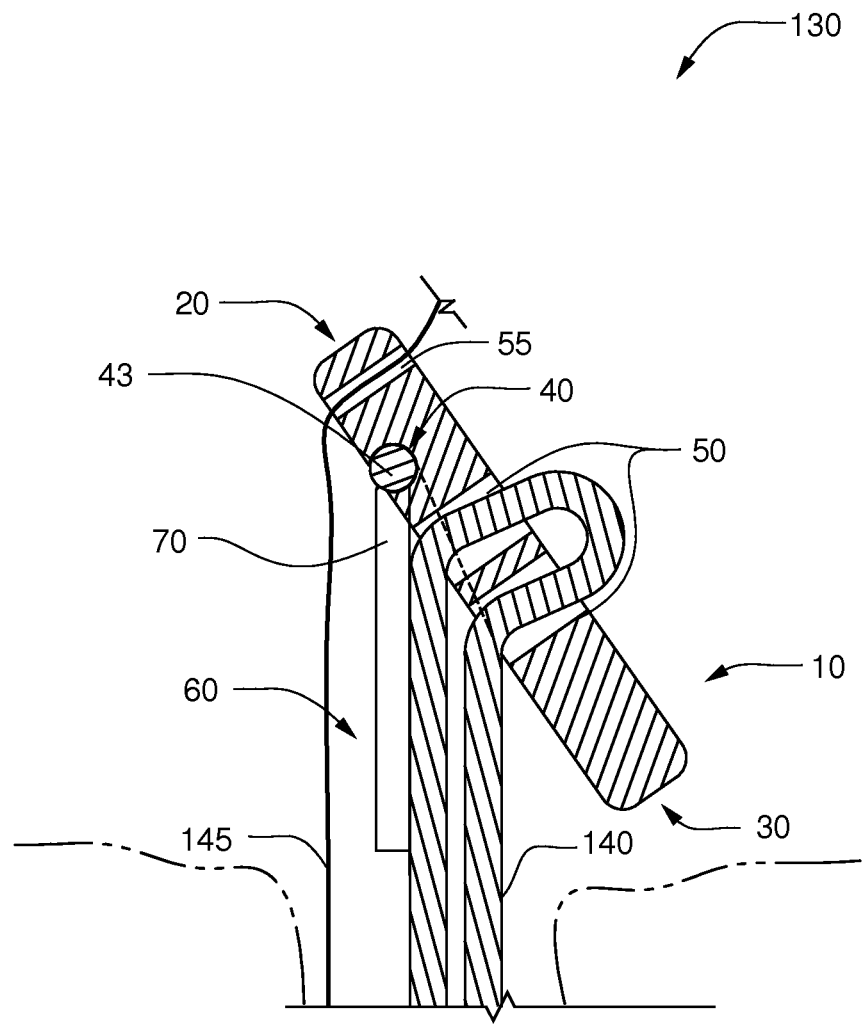
FIG. 13A is a cross-sectional view of the assembly of the toggle bolt suture anchor and toggle bolt delivery device shown in FIG. 3 as it is inserted through a drill hole in a bone.
Figure 13B:
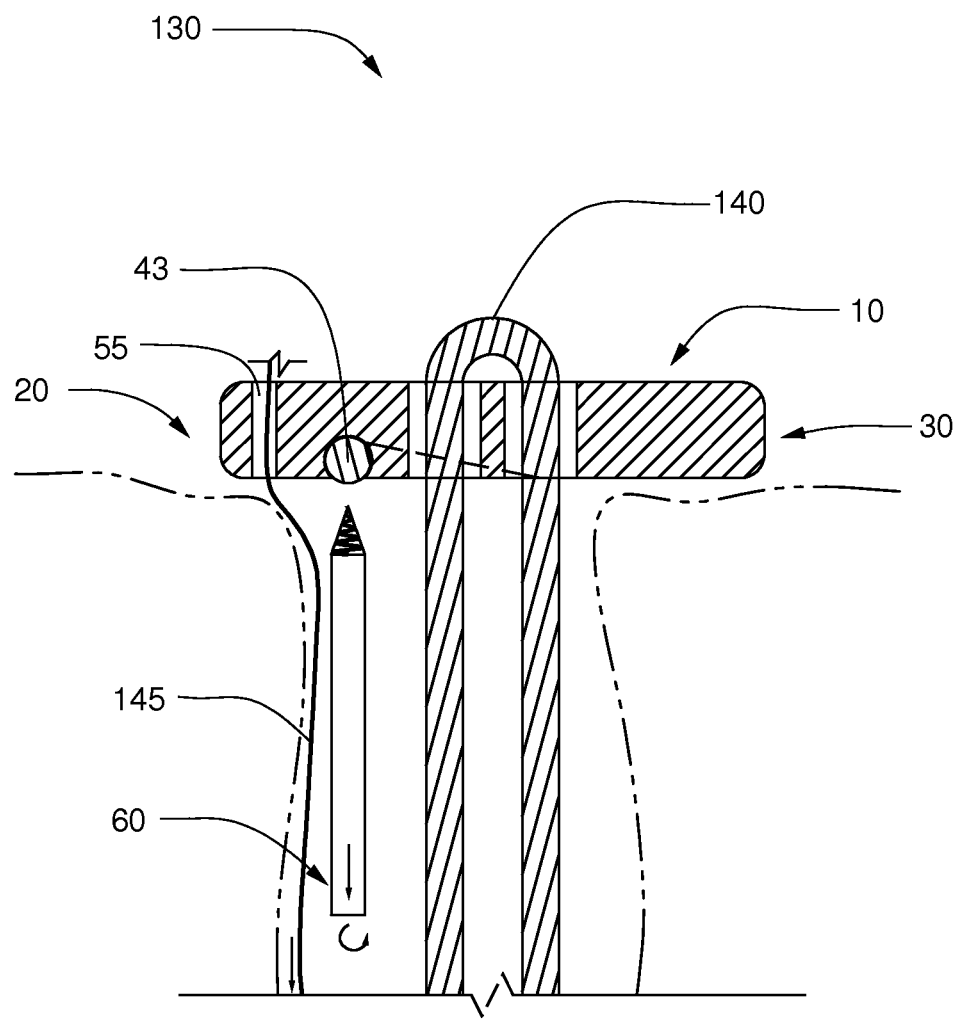
FIG. 13B is a cross-sectional view of the assembly of the toggle bolt suture anchor and toggle bolt delivery device shown in FIG. 3 after it is inserted through a drill hole and after removal of the toggle bolt delivery device from the toggle bolt.

FIGS. 13A and 13B depict the steps involved in positioning the toggle bolt suture anchor, using the assembly shown in FIG. 3, during a surgical procedure. The kit of the present invention comes with the toggle bolt suture anchor 10 attached to the toggle bolt delivery device 60 to form a toggle bolt assembly 130. The suture eyelets 50 in the toggle bolt suture anchor 10 are threaded with at least one suture thread 140. An additional suture eyelet 55 is threaded with a suture thread 145. The surgical procedure is done thorough either standard incisions or limited incisions and arthroscopically assisted. In the standard incision surgery, a drill hole is placed through the bone aiming towards the coracoid base. A second hole is drilled through the coracoid base. Visualized either directly or arthroscopically, the toggle bolt assembly 130 is inserted through the coracoid base by extending the leading edge 20 of the toggle bolt suture anchor 10 such that the suture 145 threaded through the single suture eyelet 55 (which is attached near the leading edge 20 of the toggle bolt suture anchor 10) is longer than the toggle bolt delivery device 60 (such as a threaded push pin), which is attached near the leading edge 20 of the toggle bolt suture anchor 10 at the toggle bolt delivery device interconnection means (a groove having a threaded interlocking connection) 40. The toggle bolt delivery device 60 is used to push the toggle bolt assembly 130 into position by moving along a pivot point 43 in the groove 40, causing the leading edge 20 and the trailing edge 30 of the toggle bolt suture anchor 10 to be pushed into position. In this embodiment, the lead suture 145 may be pulled to flip the trailing edge 30 of the toggle bolt suture anchor 10 into a final position where the sutures 140, 145 are parallel and the toggle bolt suture anchor 10 is perpendicular to the drill hole (see FIG. 13B). Once the toggle bolt suture anchor 10 is perpendicular to the drill hole, the toggle bolt delivery device is disengaged by twisting to remove the device from the threaded interlocking connection, and leaving the toggle bolt suture anchor 10 in position. The toggle bolt suture anchor is secured into position by tying the suture in place, typically over a bone, for example. It is understood that although the surgical method described is for an acromioclavicular repair, the method would be similar for other types of surgeries where a drill hole is made through a bone, such as a clavicle, coracoid process, proximal radius, femur, tibia, or fibula.

The above description and drawings are only illustrative of preferred embodiments which achieve the objects, features and advantages of the present invention, and it is not intended that the present invention be limited thereto. Any modification of the present invention which comes within the spirit and scope of the following claims is considered part of the present invention.

What is claimed is:

1. A toggle bolt suture anchor kit comprising: a toggle bolt delivery device and a toggle bolt suture anchor wherein the toggle bolt delivery device and the toggle bolt suture anchor are interconnectable; the toggle bolt suture anchor having an oblong body wherein the oblong body has a surface, a longitudinal axis, a leading edge and a trailing edge, a pair of suture eyelets positioned between the leading edge and the trailing edge of the oblong body, a leading suture eyelet positioned near the leading edge of the oblong body, and an at least one threaded toggle bolt delivery device interconnection means wherein the at least one threaded toggle bolt delivery device interconnection means is positioned between the leading suture eyelet and the pair of suture eyelets; and the toggle bolt delivery device having a longitudinal axis and an at least one threaded toggle bolt suture anchor interconnection means, wherein the at least one threaded toggle bolt suture anchor interconnection means is adapted for interconnection to the at least one toggle bolt delivery device interconnection means, and wherein the toggle bolt delivery device interconnection means and the toggle bolt suture anchor interconnection means form a threaded interconnection, and wherein, with the toggle bolt suture anchor interconnection means interconnected to the toggle bolt delivery device interconnection means, the toggle bolt suture anchor interconnection means is adapted to pivot, on an axis perpendicular to the longitudinal axis of the toggle bolt suture anchor, relative to the toggle bolt delivery device interconnection means.

2. The toggle bolt suture anchor kit according to claim 1, wherein the toggle bolt delivery device interconnection means forms a male-female connection with the toggle bolt suture anchor interconnection means.

3. The toggle bolt suture anchor kit according to claim 1, wherein the toggle bolt delivery device interconnection means forms an interlocking connection with the toggle bolt suture anchor interconnection means.

4. The toggle bolt suture anchor kit according to claim 1, wherein the toggle bolt delivery device interconnection means forms a screw connection with the toggle bolt suture anchor interconnection means.

5. The toggle bolt suture anchor kit according to claim 1, wherein the leading edge of the oblong body of the toggle bolt suture anchor is rounded.

6. The toggle bolt suture anchor kit according to claim 1, wherein the toggle bolt delivery device comprises a threaded push pin wherein the toggle bolt suture anchor interconnection means screws into the toggle bolt delivery device interconnection means forming a pivot connection therebetween.

7. The toggle bolt suture anchor kit according to claim 1, further comprising at least one suture thread threaded through the pair of suture eyelets positioned between the leading edge and the trailing edge of the oblong body of the toggle bolt suture anchor.

8. The toggle bolt suture anchor kit according to claim 1, wherein the toggle bolt delivery device interconnection means is a groove.

9. The toggle bolt suture anchor kit according to claim 1, wherein the toggle bolt delivery device comprises at least one wire.

10. The toggle bolt suture anchor kit according to claim 9, wherein one end of the wire has a protruded end serving as the toggle bolt suture anchor interconnection means.

11. The toggle bolt suture anchor kit according to claim 9, wherein one end of the wire is threaded and serves as the toggle bolt suture anchor interconnection means.

12. The toggle bolt suture anchor kit according to claim 1, wherein the toggle bolt delivery device interconnection means is positioned near the leading edge of the oblong body of the toggle bolt suture anchor.

13. The toggle bolt suture anchor kit according to claim 12, wherein the toggle bolt delivery device interconnection means is a groove.

14. The toggle bolt suture anchor kit according to claim 1, wherein the toggle bolt delivery device interconnection means is positioned between the leading edge of the oblong body of the toggle bolt suture anchor and the pair of suture eyelets.

15. The toggle bolt suture anchor kit according to claim 14, wherein the toggle bolt delivery device interconnection means is a groove.

16. A toggle bolt suture anchor kit comprising: a toggle bolt suture anchor having a leading edge, a trailing edge and a longitudinal axis; a toggle bolt delivery device interconnection, including a groove, positioned proximate to at least one edge of the toggle bolt suture anchor; a pair of suture eyelets positioned between the leading edge and the trailing edge of the toggle bolt suture anchor; and a leading suture eyelet positioned near the leading edge of the toggle bolt suture anchor; and a toggle bolt delivery device having a toggle bolt suture anchor interconnection including a push pin wherein the push pin is adapted to fit into the toggle bolt delivery device interconnection forming, with the toggle bolt suture anchor interconnection fit into the toggle bolt delivery device interconnection, a pivot connection, on an axis perpendicular to the longitudinal axis of the toggle bolt suture anchor therebetween; wherein the toggle bolt delivery device interconnection is positioned between the pair of suture eyelets and the leading suture eyelet.

\* \* \* \* \*